United States Patent
McMichael et al.

(10) Patent No.: US 7,549,200 B2
(45) Date of Patent: Jun. 23, 2009

(54) CLAMP FOR FLEXIBLE TUBE

(75) Inventors: Donald J. McMichael, South Jordan, UT (US); Edward B. Madsen, Riverton, UT (US); Nathan V. Shirley, Herriman, UT (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 746 days.

(21) Appl. No.: 11/139,824

(22) Filed: May 27, 2005

(65) Prior Publication Data

US 2006/0270993 A1   Nov. 30, 2006

(51) Int. Cl.
*F16K 7/06* (2006.01)
(52) U.S. Cl. .......................... 24/518; 24/132 R; 24/910
(58) Field of Classification Search .................. None
See application file for complete search history.

(56) References Cited

U.S. PATENT DOCUMENTS

| | | | |
|---|---|---|---|
| 3,253,594 A | 5/1966 | Matthews et al. |
| 3,397,699 A | 8/1968 | Kohl |
| 4,077,412 A | 3/1978 | Moossun |
| 4,315,513 A | 2/1982 | Nawash et al. |
| 4,393,873 A | 7/1983 | Nawash et al. |
| 4,516,968 A | 5/1985 | Marshall et al. |
| 4,666,433 A | 5/1987 | Parks |
| 4,668,225 A | 5/1987 | Russo et al. |
| 4,677,967 A | 7/1987 | Zartman |
| 4,685,901 A | 8/1987 | Parks |
| 4,769,004 A | 9/1988 | Poindexter |
| 4,861,334 A | 8/1989 | Nawaz |
| 4,986,810 A | 1/1991 | Semrad |
| 5,073,166 A | 12/1991 | Parks et al. |
| 5,112,310 A | 5/1992 | Grobe |
| 5,183,464 A | 2/1993 | Dubrul et al. |
| 5,232,440 A | 8/1993 | Wilk |
| 5,234,454 A | 8/1993 | Bangs |
| 5,267,968 A | 12/1993 | Russo |
| 5,273,529 A | 12/1993 | Idowu |
| 5,275,610 A | 1/1994 | Eberbach |
| 5,279,564 A | 1/1994 | Taylor |
| 5,290,249 A | 3/1994 | Foster et al. |
| 5,318,542 A | 6/1994 | Hirsch et al. |
| 5,356,391 A | 10/1994 | Stewart |
| 5,358,488 A | 10/1994 | Suriyapa |
| 5,431,676 A | 7/1995 | Dubrul et al. |
| 5,439,444 A | 8/1995 | Andersen et al. |
| 5,443,449 A | 8/1995 | Buelna |
| 5,484,420 A | 1/1996 | Russo |
| 5,507,279 A | 4/1996 | Fortune et al. |
| 5,549,657 A | 8/1996 | Stern et al. |

(Continued)

FOREIGN PATENT DOCUMENTS

EP    1025802 A1    8/2000

(Continued)

*Primary Examiner*—Jack W. Lavinder
(74) *Attorney, Agent, or Firm*—Sue C. Watson

(57) ABSTRACT

A clamp for use with a flexible tube is disclosed. The clamp has a first and a second body portion each having a channel positioned upon a surface of the body portion. A detent mechanism is provided for securing the first and second body portions together such that the channel in one body portion aligns with the channel in the other body portion forming a passage through the clamp.

12 Claims, 3 Drawing Sheets

U.S. PATENT DOCUMENTS

| | | | |
|---|---|---|---|
| 5,860,960 A | 1/1999 | Quinn | |
| 6,039,714 A | 3/2000 | Cracauer et al. | |
| 6,090,073 A | 7/2000 | Gill | |
| 6,186,985 B1 | 2/2001 | Snow | |
| 6,322,538 B1 | 11/2001 | Elbert et al. | |
| 6,387,076 B1 * | 5/2002 | Landuyt | 604/174 |
| 6,402,722 B1 | 6/2002 | Snow et al. | |
| 6,458,106 B1 | 10/2002 | Meier et al. | |
| 6,471,676 B1 | 10/2002 | Delegge et al. | |
| 6,482,183 B1 * | 11/2002 | Pausch et al. | 604/174 |
| 6,582,395 B1 | 6/2003 | Burkett et al. | |
| 6,673,058 B2 | 1/2004 | Snow | |
| 6,743,207 B2 | 6/2004 | Elbert et al. | |
| 6,765,122 B1 | 7/2004 | Stout | |
| 6,769,546 B2 | 8/2004 | Busch | |
| 7,264,609 B2 | 9/2007 | Hakky et al. | |
| 2002/0169360 A1 | 11/2002 | Taylor et al. | |
| 2004/0092796 A1 | 5/2004 | Butler et al. | |
| 2004/0097794 A1 | 5/2004 | Bonutti | |
| 2004/0193114 A1 | 9/2004 | Elbert et al. | |
| 2005/0216040 A1 | 9/2005 | Gertner et al. | |
| 2005/0267520 A1 | 12/2005 | Modesitt | |

FOREIGN PATENT DOCUMENTS

| | | |
|---|---|---|
| EP | 1077057 B1 | 7/2004 |
| WO | WO 97/25095 | 7/1997 |
| WO | WO 98/19730 | 5/1998 |
| WO | WO 98/26720 | 6/1998 |
| WO | WO 00/50110 | 8/2000 |
| WO | WO 02/058594 | 8/2002 |
| WO | WO 02/066108 | 8/2002 |
| WO | WO 03/092780 | 11/2003 |
| WO | WO 03/094826 | 11/2003 |
| WO | WO 2005/110280 | 11/2005 |

* cited by examiner

CLAMP FOR FLEXIBLE TUBE

BACKGROUND OF THE INVENTION

The present invention relates to a clamp and, more particularly to a clamp adapted to secure a flexible tube from longitudinal and rotational movement with respect to the clamp. A clamp of this form may prove useful as an external anchoring device for cannulae such as used in the percutaneous placement of various catheters such as gastrostomy and/or Jejunostomy tubes.

For example, numerous medical conditions exist in which it becomes necessary to gain percutaneous access to viscera such as the stomach or small intestines. Situations where a patient has lost the ability to swallow and will require long term nutritional support may dictate feeding directly into the stomach or jejunum. This type of feeding may be accomplished by inserting a feeding tube into the patient's stomach such that one end remains anchored in the stomach, while the other end remains external to the patient's body for connection to a nutrient source. Once such a tube is in place, the portion of the tube extending outside the abdominal wall must have any material flows therethrough controlled. Additionally, it is important that the tube remain in place and not be drawn any further into the stomach once it is positioned. Typically, a clamp is used on the flexible tube to permit or deny flow therethrough as desired as well as to secure the tube against further entry into the stomach.

Prior to the placement of the feeding tube a stoma between the stomach lumen and the external environment is created through the abdominal wall. This process is accomplished by way of a gastropexy procedure. This procedure enables the physician to attach the visceral wall to the abdomen. The attachment is critical to prevent inadvertent separation and exposure of the peritoneal cavity to contamination and possible peritonitis. This procedure is also applicable to Jejunostomy or Gastro-Jejunostomy as well as the Gastrostomy procedure referred to above. The external retention anchors or clamps used in these procedures typically include locking rings which are situated next to the patient's skin. Often times the use of these locking rings require significant manipulation on the part of the surgical technician for proper placement. In some prior art devices, the exterior of the gastrostomy tube is taped to the wearer's body, and this can cause infection at the stoma entry, and along the taped area, as well as causing irritation due to the difficulty in maintaining these areas clean.

What is needed is a fixation device that is easy to place externally to the patient's skin that positively locks with respect to the cannula.

SUMMARY OF THE INVENTION

In response to the foregoing problems and difficulties encountered by those of skill in the art, the present invention is directed toward a clamp. The clamp has a first and a second body portion. The first body portion contains a first major surface formed by a coplanar surface of each of a first arm, a second arm, and a yoke connecting the first arm to the second arm. The first body portion also contains a second major surface formed by an additional surface of each of the first arm, the second arm, and the yoke. The second major surface is disposed substantially normal to the first major surface. A yoke surface is positioned opposite the second major surface and disposed between the first and second arms. A recess is contained within the yoke surface and it extends across the first major surface and terminates at the second major surface. The second body portion also contains a first major surface, a second major surface disposed substantially normal to the first major surface, and a cantilevered arm extending normal to the first major surface which is situated a distance from the first major surface. A recess is formed within a surface of the cantilevered arm, the recess extends across the first major surface and terminates at the second major surface. The clamp also contains a hinge connecting the first body portion to the second body portion so that the first major surfaces of each of the first and second body portions are contiguous to one another and the recesses within each of the first and second body portions form a passage through the clamp.

In certain embodiments the following variations are contemplated either alone or in various combinations: the hinge is a living hinge; the cantilevered arm is provided with a flanged end for engaging and locking securely with the first and second arms; the second major surfaces of both of the first and the second body portions form a smooth curvilinear surface when conjoined so as to seat comfortably against a patient's skin; gripping elements are placed within the passage; and the clamp may be made to be permanent so that it must be destroyed in order to be removed.

In other embodiments, the invention is directed to a clamp having a first and a second body portion. The first body portion having two parallel arms separated one from the other by a channel. The first body portion also contains a first major surface normal to the channel which and abutting both arms. A recess is formed within the channel extending over the first major surface and terminating at a second major surface. The second body portion also contains a first major surface, a cantilevered arm extending normal to the first major surface, and a recess within the cantilevered arm extending over the first major surface. The recess terminates at a second major surface. The cantilevered arm is adapted to engage the channel and lock between the parallel arms placing the first major surfaces contiguous to one another such that the recesses align to form a passage through the clamp.

In certain embodiments the following variations as well as the variations specified above are contemplated either alone or in various combinations: a hinge may be provided connecting the first body portion with the second body portion; gripping elements may be formed within the passage; the passage may be nonlinear; the second major surfaces when joined form a smooth clamp surface having rounded perimetrical edges; and the clamp is adapted to secure a flexible tube within the passage and inhibit the tube from longitudinal and rotational movement with respect to the clamp.

In other embodiments, the invention is directed to a clamp having a first and a second body portion each having a channel positioned upon a surface of the body portion. A detent mechanism is provided for securing the first and second body portions together such that the channel in one body portion aligns with the channel in the other body portion forming a passage through the clamp.

In certain embodiments the following variations as well as the variations specified above are contemplated either alone or in various combinations: the passage through the clamp may be linear or nonlinear; the detent mechanism may consist of a cantilevered arm captured between a pair of opposing arms; the detent mechanism may be selectively releasable; the detent mechanism once engaged may be releasable only through destruction of the clamp; the first and second body portions are hingedly fastened to one another and adapted to engage with one another by application of force applied by one hand.

Other objects, advantages and applications of the present invention will be made clear by the following detailed description of a preferred embodiment of the invention and the accompanying drawings wherein reference numerals refer to like or equivalent structures.

DETAILED DESCRIPTION OF THE PRESENT INVENTION

Figure 2:
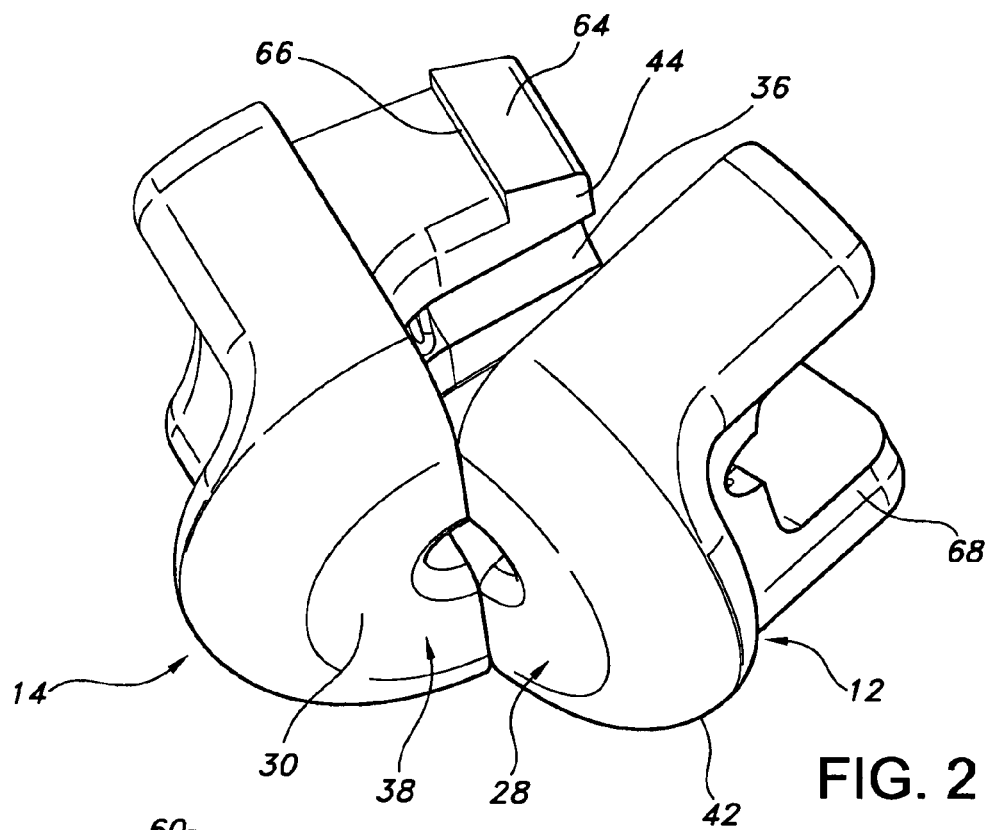
FIG. 2 is an isometric view of the FIG. 1 clamp viewed from the second major surfaces.

In response to the foregoing challenges that have been experienced by those of skill in the art, the present invention is directed toward a clamp for use in inhibiting a flexible tube from both longitudinal and rotational movement with respect to the clamp. In one embodiment, as depicted on FIG. 1, such a clamp 10 is provided. In this embodiment, the clamp 10 includes a first body portion 12 and a second body portion 14. The first body portion 12 includes a first major surface 16; likewise the second body portion 14 includes a corresponding first major surface 18.

In the embodiment shown, the first body portion 12 may contain two arms 20 connected by a yoke 22. The arms 20 and yoke 22 may be formed by placement of a channel 24 through a region of the first body portion 12. The first major surface 16 in this instance would consist of a coplanar surface formed by: the surface 16a of the first arm 20a, the surface 16b of the second arm 20b, and the surface 16c of the yoke 22. The second body portion 14 may contain a cantilevered arm 26 extending from the first major surface 18 capable of being inserted between the two arms 20a and 20b.

Although the above described embodiment specifies the use of one cantilevered arm 26 engaging two arms 20, this is not a requirement. It should be understood that any number of arms 26 may be provided to interact and engage with any number of arms 20 depending upon ease of manufacture as well as other design considerations.

Figure 1:
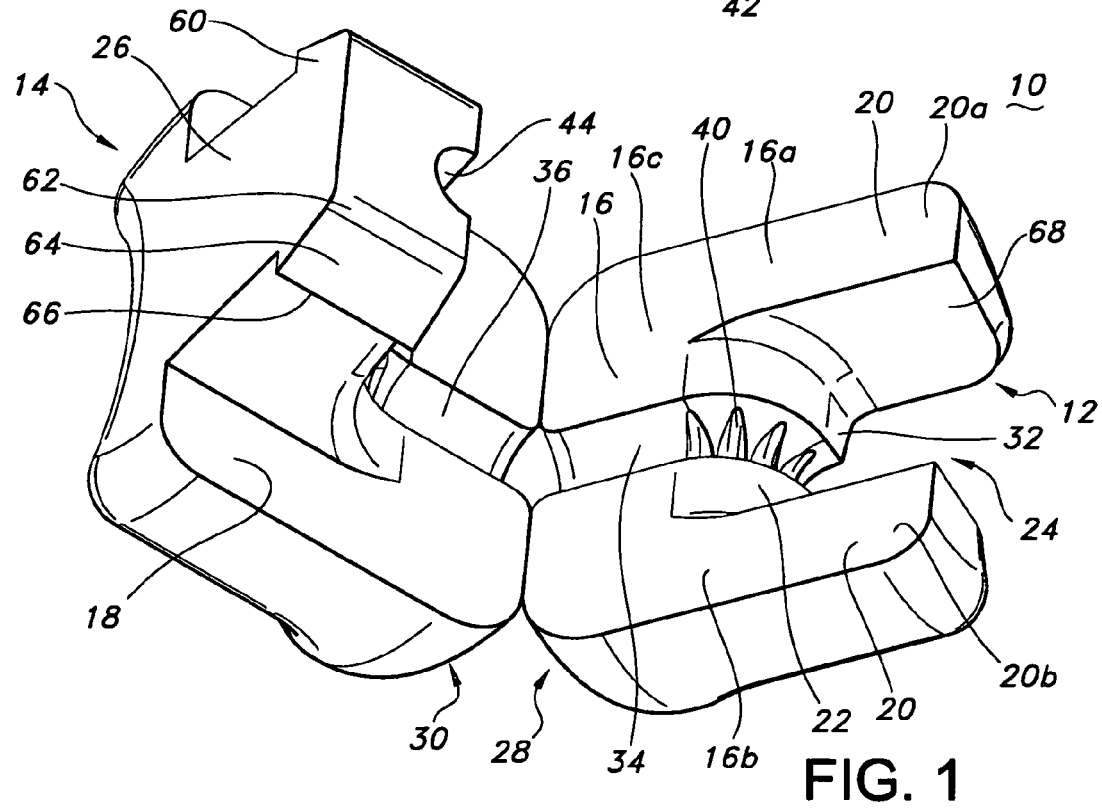
FIG. 1 is an isometric view of a clamp according to the present invention viewed from the first major surfaces.

Looking again to the embodiment of FIG. 1. it may be seen that a second major surface 28 is formed by an additional surface of the first body portion 12. The second major surface 28 is disposed substantially normal to the first major surface 16. The yoke 22 may be further characterized in that it also contains a yoke surface 32 which intersects with the surface 16c. A recess 34 is situated in the yoke surfaces 16c and 32 and as such may be seen to extend from the yoke surface 32, continue across a portion of the first major surface 16, and terminate at the second major surface 28 of the first body portion 12.

Likewise the second body portion 14 includes a second major surface 30 substantially normal to the first major surface 18. Also the cantilevered arm 26 includes a surface 44. A recess 36 is situated in the second body portion 14 as well. As such the recess 36 may be seen to extend from the surface 44, continue across a portion of the first major surface 18, and terminate at the second major surface 30 of the second body portion 14.

As may be seen in FIG. 2, the first and second body portions 12, 14 may be connected to one another by a hinge 38.

A number of potential hinge configurations may prove useful, would be known and understood by those of skill in the art, and as such are not specifically enumerated. Some simple hinge configurations that might prove useful but are in no way meant as limitations include living hinges and continuous or piano-type hinges. In the event that the first and second body portions 12, 14 are manufactured of a flexible plastic such as polypropylene or polyethylene, a living hinge would prove extremely useful in that it would not require a separate and distinct component be affixed to each of the body portions 12, 14.

Although the hinge 38 is illustrated as being located at the second major surfaces 28 and 30 respectively, there is no reason that the hinge be confined to these surfaces. In fact, the hinge 38 if provided, may be located at any position that enables the first body portion 12 to engage with the second body portion 14. Alternatively, the first body portion 12 may engage the second body portion 14 by the coupling of alternative fastening mechanisms. Fasteners such as bayonet type fasteners, tabs engaging receiving slots, and other locking mechanisms are contemplated as well.

Figure 3:
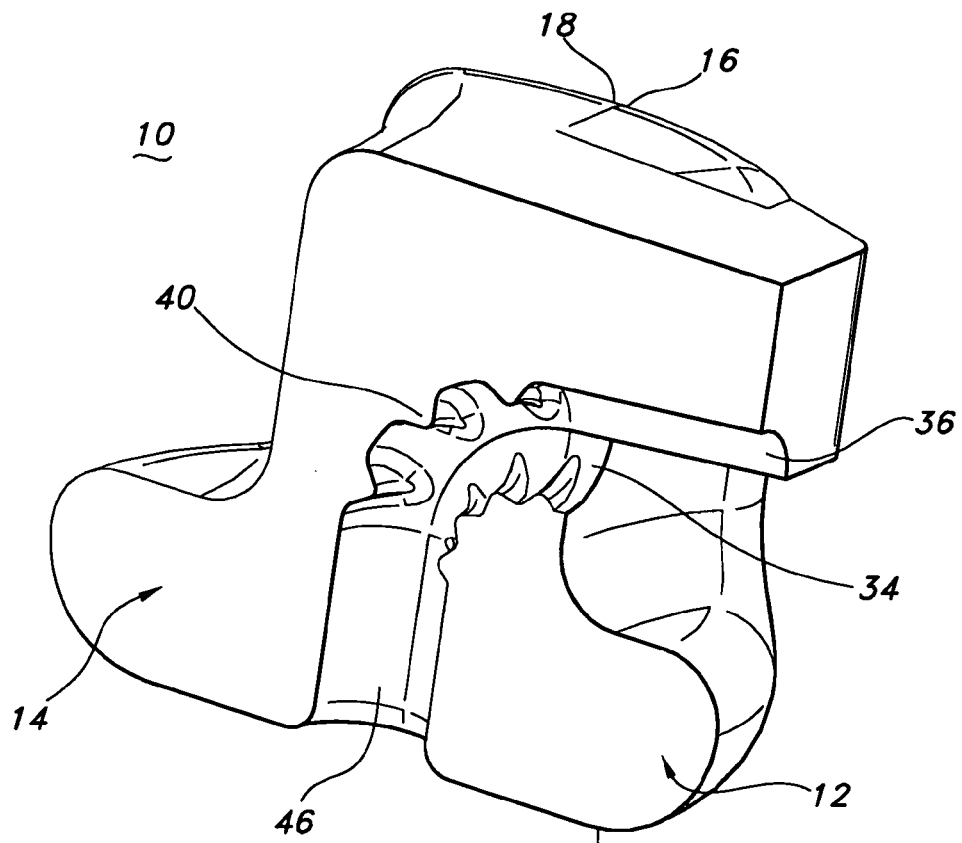
FIG. 3 is a cutaway of the FIG. 1 clamp viewed through the center of the clamp so as to depict the passage therethrough.

Looking now to the FIG. 3 sectional view, closing or engaging the first body portion 12 with the second body portion 14 by engaging the cantilevered arm 26 with the arms 20 places the first major surface 16 contiguous to the first major surface 18. As such, the recesses 34 and 36 are placed in alignment as well and cooperate to form a passage 46 through the clamp 10. Due to the configuration of the body portions 12 and 14 as described above, in this embodiment, it should be evident that the passage 46 through the clamp 10 is nonlinear. A plurality of gripping elements 40 may be provided in either or both of the recesses 34 and/or 36 to increase friction between the clamp 10 and a flexible tube ultimately inserted into or through the passage 46. The gripping elements 40 may comprise a textured surface formed by the addition of teeth, crenations, corrugations, or the like. In an alternative embodiment, a surface treatment such as a coating, a textured surface, or a combination of both may prove useful in increasing the gripping force or friction between the sidewalls of the passage 46 and the flexible tube.

One use for such an embodiment as the one described above would be as a clamp adapted for use in the medical field. For example, the clamp 10 may prove useful to secure a flexible tube such as surgical tubing, a catheter, or other cannula against both longitudinal and axial movement, that is movement along the axis of the tube and movement about the axis of the tube respectively.

A clamp in accordance with the present invention may be desirable for use in a gastropexy procedure. This procedure enables the physician to attach the visceral wall to the abdomen through the use of a bolster or other anchor that is positioned within the stomach lumen. This attachment is critical to prevent inadvertent separation and exposure of the peritoneal cavity to contamination and possible peritonitis. Such a procedure is depicted in FIG. 4.

Figure 4:
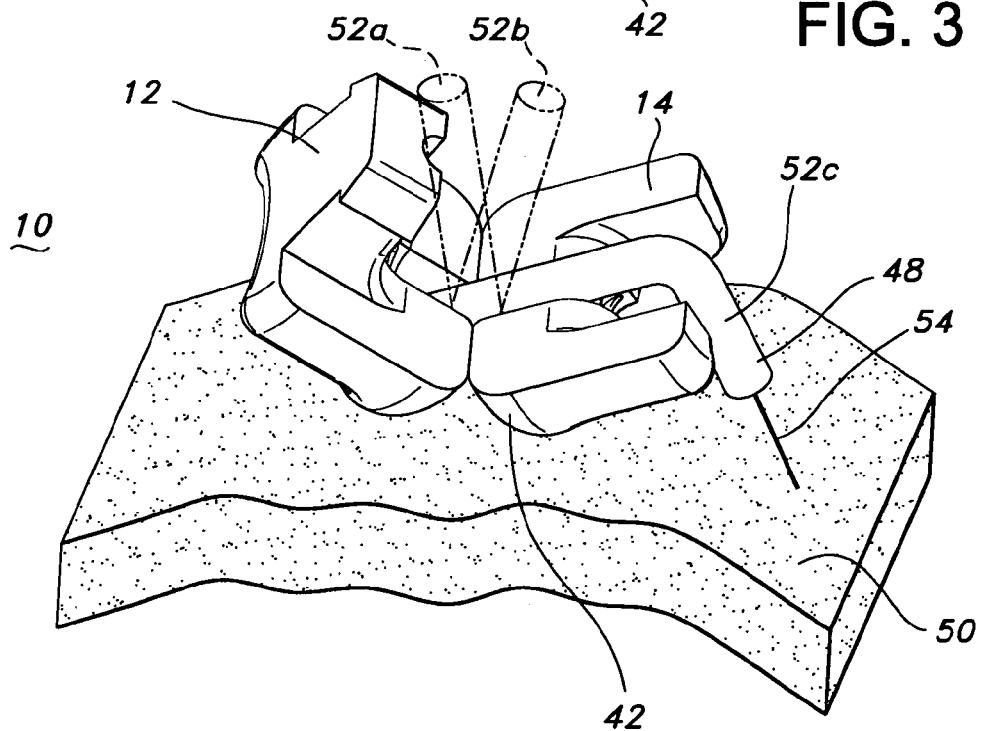
FIG. 4 is a diagrammatic illustration of the FIG. 1 clamp in use.

As shown in FIG. 4, a cannula 48 is depicted as having been positioned in a patient, for example, through the abdominal wall 50. Once the stomach lumen (not shown) and the abdominal wall 50 have been brought into the desired degree of contact, the first and second body portions 12 and 14 of the clamp 10 may be engaged with one another. As the clamp is engaged, the cannula 48 is forced into the recesses 34 and 36 within the body portions 12 and 14 and bent from its first substantially linear configuration 52a to its final nonlinear configuration 52c after having progressed through a series of intermediate positions designated simply as 52b.

When the body portions 12 and 14 of the clamp 10 are fully engaged, the cannula 48 is seated within the passage 46 formed by the recesses 34 and 36. As such, the cannula 48 is secured against both longitudinal and rotational movement with respect to the clamp 10. Moreover, cooperation between the anchor situated internal to the patient's body and the clamp 10 external to the abdominal wall 50 secures the cannula 48 in position until such time that the surgical team is satisfied with the progress in the creation of the stoma. By providing the rounded perimetrical edge 42, the clamp 10 is adapted for seating against a patient's body in a comfortable less irritating manner than other prior art devices.

In some embodiments, a cable, wire, or equivalent may be associated with the cannula 48. Such a wire 54 may be used to engage the anchor situated within the stomach or other body lumen as disclosed in co-pending application filed on May 27, 2005 under US Express Mail Number EV 064854687US to McMichael et al., which is incorporated herein by reference in its entirety. The clamp 10 should have sufficient clamping force to ensure that the wire 54 remains stationary within the cannula 48.

To provide the surgical team with an easily used clamp, the body portion 14 may be provided with a thumb seat 56 whereas the body portion 12 may be provided with one or more finger seats 58. This enables the operator to place the thumb of his first hand on the thumb seat 58 while grasping the cannula 48 with his second hand. By placing the fingers of his first hand on the finger seat or seats 58 and drawing them toward his thumb, the clamp 10 may be fastened thus securing the cannula 48 as described above. The thumb and finger seats 56 and 58 respectively, may be contoured and/or textured to more naturally conform to the shape of the user's hand as well as to increase friction between the clamp 10 and the user's hand. Optionally, the thumb and finger seats 56 and 58 may be coated with a material to increase friction. This may be done in addition to or in lieu of texturing the surface.

In many embodiments, for example, in the embodiments depicted in FIGS. 1-4, the clamp 10 is designed to be permanently fastened. That is, in order to disengage the clamp, it must be destroyed. Looking again to FIGS. 1 and 2, the cantilevered arm 26 comprises oppositely oriented locking flanges 60. Each flange 60 may comprise a leading edge 62, a cam surface 64, and a locking tab 66. In the depicted embodiment, the leading edge 62 of the flange 60 is contacted with opposing arm surface 68 disposed upon each arm 20. Continued application of force causes the cam surfaces 64 to spread or otherwise separate the arms 20 slightly until the cam surface is clear at which time the locking tab 66 engages a land 68 located on the first body portion 12. To remove the clamp 10, an inherently weakened region may be provided. One such region may be at the hinge 38; another may be at any of the arms 20 or cantilevered arm 22. In any event, specific regions of weakness may be incorporated into the clamp. Alternatively, the cannula may be severed between the patient's abdomen and the second major surfaces 28 and 30. Once severed, that portion of the cannula internal to the patient's body may be withdrawn through the abdominal wall, endoscopically, or allowed to pass naturally through the body as appropriate.

Figure 5:
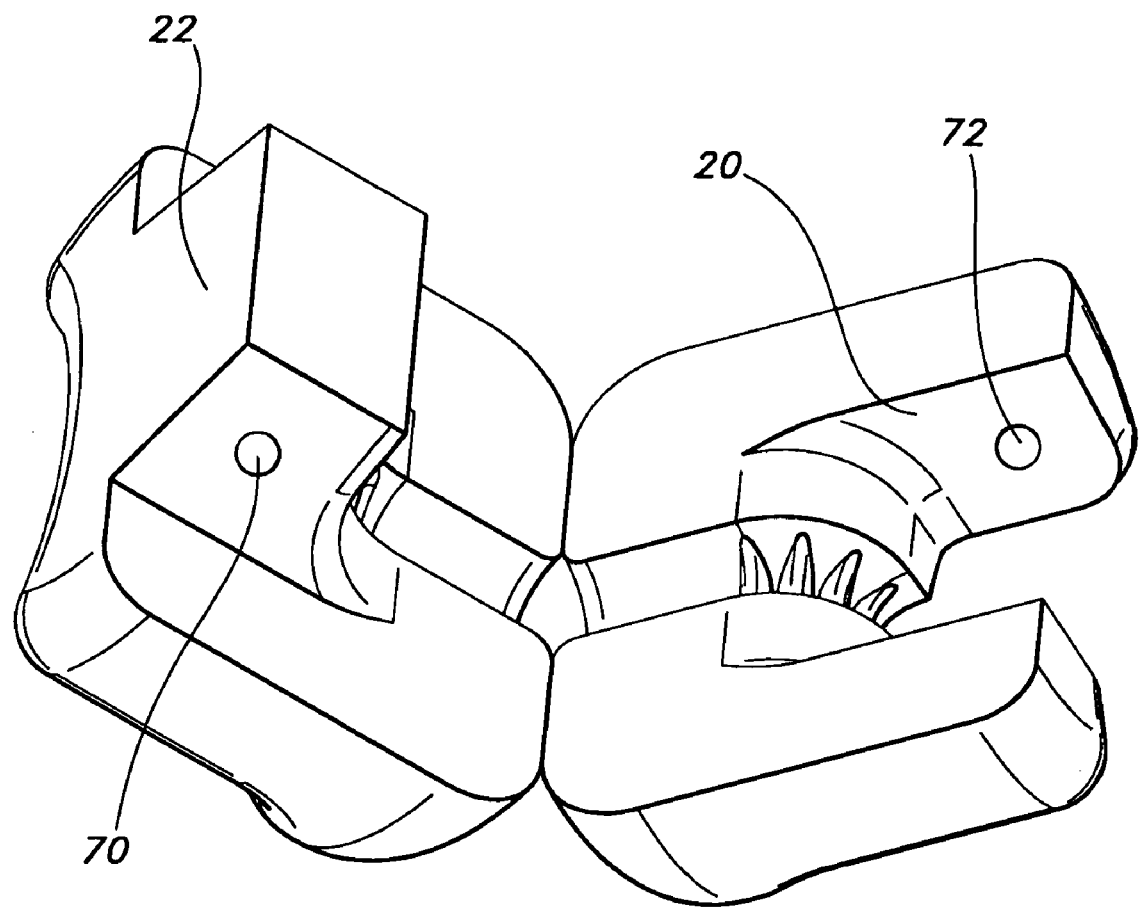
FIG. 5 is an isometric view of an alternative clamp according to the present invention viewed from the first major surfaces, depicting a releasable detent mechanism.

An alternative embodiment depicted in FIG. 5 may be similar in many of the features described in FIGS. 1-4, however in this embodiment the clamp may be reversibly fastened. One mechanism that may prove useful in a reversible clamp is a detent mechanism. Such a mechanism may comprise a spring biased protrusion such as a ball 70 placed on the cantilevered arm 22. The ball engages a matching socket 72 placed on the arm 20. In order to overcome the seating force of the ball within the socket, a greater force would be needed to disengage the clamp. Such devices are well known. It should be noted that in this configuration the ball engages with the socket, however the ball 70 may be disposed in either arm 20 or 22. Additionally, more than one ball and socket detent mechanism may be provided as well.

Furthermore, any detent mechanism comprising a catch or lever that reversibly locks and unlocks the movement of one part of the mechanism with respect to the other would serve the purpose described above. As such the specific configuration would be dependent upon the desired use of the clamp 10 and therefore would be easily designed by one of skill in the art upon reading of this specification.

As used herein and in the claims, the term "comprising" is inclusive or open-ended and does not exclude additional unrecited elements, compositional components, or method steps.

While various patents have been incorporated herein by reference, to the extent there is any inconsistency between incorporated material and that of the written specification, the written specification shall control. In addition, while the invention has been described in detail with respect to specific embodiments thereof, it will be apparent to those skilled in the art that various alterations, modifications and other changes may be made to the invention without departing from the spirit and scope of the present invention. It is therefore intended that the claims cover all such modifications, alterations and other changes encompassed by the appended claims.

We claim:

1. A clamp comprising:
   a first body portion having;
      a first major surface formed by a coplanar surface of each of a first arm, a second arm, and a yoke connecting the first arm to the second arm,
      a second major surface formed by an additional surface of each of the first arm, the second arm, and the yoke, the second major surface being disposed substantially normal to the first major surface,
      a yoke surface positioned opposite the second major surface and disposed between the first and second arms, and
      a recess within the yoke surface, extending across the first major surface, and terminating at the second major surface;
   a second body portion having;
      a first major surface,
      a second major surface disposed substantially normal to the first major surface,
      a cantilevered arm extending normal to the first major surface and situated a distance from the first major surface,
      a recess within a surface of the cantilevered arm, extending across the first major surface, and terminating at the second major surface; and
   a hinge connecting the first body portion to the second body portion so that the first major surfaces of each of the first and second body portions are contiguous to one another and the recesses within each of the first and second body portions form a passage through the clamp.

2. The clamp of claim 1 wherein the hinge comprises a living hinge.

3. The clamp of claim 1 wherein the cantilevered arm comprises a flanged end for engaging and locking securely with the first and second arms.

4. The clamp of claim 1 comprising a smooth curvilinear surface over the conjoined second major surfaces of both of the first and the second body portions.

5. The clamp of claim 1 comprising gripping elements within the passage.

6. The clamp of claim 1 wherein the clamp is adapted to be destructively released after engaging the cantilevered arm with the first and second arms.

7. A clamp comprising:
   a first body portion having two parallel arms separated one from the other by a channel, a first major surface normal to the channel and forming a top surface of the arms, and a recess within the channel extending across and along the first major surface and terminating at a second major surface; and
   a second body portion having a first major surface, a cantilevered arm extending normal to the first major surface, and a recess within the cantilevered arm extending along and across the first major surface and terminating at a second major surface; wherein the cantilevered arm is adapted to engage the channel and lock between the parallel arms placing the first major surfaces contiguous to one another such that the recesses align to form a passage through the clamp.

8. The clamp of claim 7 comprising a hinge connecting the first body portion with the second body portion.

9. The clamp of claim 7 comprising gripping elements within the passage.

10. The clamp of claim 7 wherein the passage is nonlinear.

11. The clamp of claim 7 wherein each of the second major surfaces when joined, form a smooth clamp surface having rounded perimetrical edges.

12. The clamp of claim 7 adapted to secure a flexible tube within the passage and inhibit the tube from longitudinal and rotational movement with respect to the clamp.

* * * * *